United States Patent [19]
Domanski et al.

[11] Patent Number: 6,056,711
[45] Date of Patent: May 2, 2000

[54] ADJUSTABLE CERVICAL COLLAR

[75] Inventors: Edward M. Domanski, Cincinnati; Sherry A. Hinds, Goshen; Richard G. Taylor, Cincinnati, all of Ohio

[73] Assignee: Beiersdorf, Inc., Cincinnati, Ohio

[21] Appl. No.: 08/882,987

[22] Filed: Jun. 26, 1997

[51] Int. Cl.[7] .................................................... A61F 5/00
[52] U.S. Cl. ........................................ 602/18; 128/DIG. 23
[58] Field of Search .............. 602/17–19; 128/DIG. 23, 128/97.1

[56] References Cited

U.S. PATENT DOCUMENTS

| | | | |
|---|---|---|---|
| 3,024,784 | 3/1962 | Monfardini . | |
| 3,374,785 | 3/1968 | Gaylord, Jr. | 602/18 |
| 3,477,425 | 11/1969 | Grassl | 602/18 |
| 3,512,523 | 5/1970 | Barnett | 602/18 |
| 3,696,810 | 10/1972 | Gaylord et al. . | |
| 3,850,164 | 11/1974 | Hare . | |
| 3,916,884 | 11/1975 | Attenburrow | 602/18 |
| 3,921,626 | 11/1975 | Neel | 602/18 |
| 4,232,663 | 11/1980 | Newton | 602/18 |
| 4,576,150 | 3/1986 | Auracher | 602/18 |
| 4,582,051 | 4/1986 | Greene et al. | 602/18 |
| 4,712,540 | 12/1987 | Tucker et al. . | |
| 4,819,622 | 4/1989 | Taylor et al. | 602/18 |
| 4,827,915 | 5/1989 | Gorsen | 602/18 |
| 4,966,136 | 10/1990 | Bates . | |
| 4,987,891 | 1/1991 | Gaylord, Jr. et al. | 602/18 |
| 5,058,572 | 10/1991 | Schmid et al. . | |
| 5,211,623 | 5/1993 | Sarkozi . | |
| 5,295,949 | 3/1994 | Hathaway | 602/18 |
| 5,403,266 | 4/1995 | Bragg et al. | 602/18 X |
| 5,520,619 | 5/1996 | Martin | 602/18 |
| 5,593,382 | 1/1997 | Rudy, Jr. et al. | 602/18 |

FOREIGN PATENT DOCUMENTS 2582936  12/1986  France ...................................... 602/18

*Primary Examiner*—Linda C. Dvorak
*Attorney, Agent, or Firm*—Frost & Jacobs LLP

[57] ABSTRACT

A fully adjustable cervical collar can be adjusted not only in overall length but also in height. The height of the collar is adjusted by releasably compressing the core material of the collar.

25 Claims, 3 Drawing Sheets

ADJUSTABLE CERVICAL COLLAR

BACKGROUND

The present invention relates to an adjustable cervical collar. More particularly, it relates to a cervical collar that is adjustable not only in overall length, but also in height.

FIELD OF THE INVENTION

Use of cervical collars is prescribed by physicians in treating trauma of the muscles and ligaments of the neck, and of the cervical and upper thoracic vertebrae and associated spinal nerves. The collar, by shifting support of the head from the neck and vertebrae to the lower chin and upper sternum, allows the effected body parts to maintain a substantially neutral and relaxed position and thus, heal faster and more completely.

It is well known to provide a cervical collar having an adjustable circumference. This allows one size collar to be adapted for use by individuals with varying neck circumferences. However, just as different individuals have different neck circumferences, they also have different neck lengths. It is desirable to have a cervical collar that is fully adjustable so that it can fit most individuals. A filly adjustable collar is adjustable not only in circumference but also in height.

U.S. Pat. No. 3,916,885, issued on Nov. 4, 1975, to Gaylord, describes an adjustable cervical collar made from an Overlapping pair of semi-rigid plastic bands. Movement of the bands relative to one another adjusts the height of the collar. Adjustable Velcro® straps are used to hold these moveable bands in place relative to one another and, therefore, fix the height of the collar. The collar is made from semi-rigid material which is not compressible.

U.S. Pat. No. 3,034,784, issued on Mar. 13, 1962, to Monfardini, describes an adjustable cervical collar which is made from a single piece of semi-rigid plastic material. The collar has an elongated slit running along its length which essentially splits the collar into lower and upper halves. The height of the collar is adjusted by moving the halves toward each other or away from each other. The halves are held in place by metal strips which run across the slit and can be tightened once the desired height is achieved. Height adjustment is not obtained by compression of the collar material itself.

U.S. Pat. No. 5,211,623, issued on May 18, 1993, to Sarkozi, describes a self-adjusting soft neck support collar comprising a sleeve made from a flexible knit material holding tubular elements which go around the neck providing support. The tubular elements are soft-filled, although most of the materials disclosed for that use are not elastic. The height adjustment of the collar is made by changing the diameter of the tubular elements which are inserted into the fabric sleeve. The height adjustment is also based on the firmness of the tubular elements used. There is no element in this collar which holds the height of the collar in a compressed state as a means for adjusting its height.

U.S. Pat. No. 4,966,136, issued on Oct. 30, 1990, to Bates, describes an orthopaedic support device which may take the form of a soft cervical collar. The device consists of a resilient foam pad covered by a fabric material. The fabric cover includes a Velcro® strip sewn along its length. This strip, in conjunction with a Velcro® strap attached at the end of the collar, is used to adjust the length (i.e. circumference) of the collar. The height of the collar is not adjustable in use. The patent discloses a band which is used to compress the width of the foam to a set dimension while the collar is being assembled, however, that band is not present in the finished product. It cannot be used to vary the width of the collar, but merely to maintain a uniform width as the device is being assembled.

The present invention provides a cervical collar having a means of adjusting its height by compressing the collar material. Unlike the prior art, the present invention does not require movement of a portion of the collar relative to another portion of the collar for height adjustment. Furthermore, the present invention is not made of a semi-rigid material as disclosed in the prior art, but rather is a soft, compressible material. The collar of the present invention, therefor, is not only adjustable to fit most wearers, but is also relatively easy and inexpensive to manufacture.

SUMMARY OF THE INVENTION

The present invention provides a cervical collar comprising:

an elongated body member comprising a compressible core and a fabric covering substantially enclosing said core and conforming substantially to the configuration thereof, said body member having a medial portion and end portions at opposite ends of the medial portion;

fastening means for adjustably securing said body member in encircling relation to a wearer's neck; and a height adjusting band attached to and encircling the medial portion of said body member, said height adjusting band being capable of releasably and adjustably holding the height of said medial portion in a compressed condition.

DETAILED DESCRIPTION OF THE PREFERRED EMBODIMENT

The present invention provides a fully adjustable therapeutic cervical collar having a strategically located strap which enables height adjustment of the collar according to the wearer's neck length. The collar can be tailored to fit at least 95% of the general population as dictated by standard anthropometric data.

Figure 1:
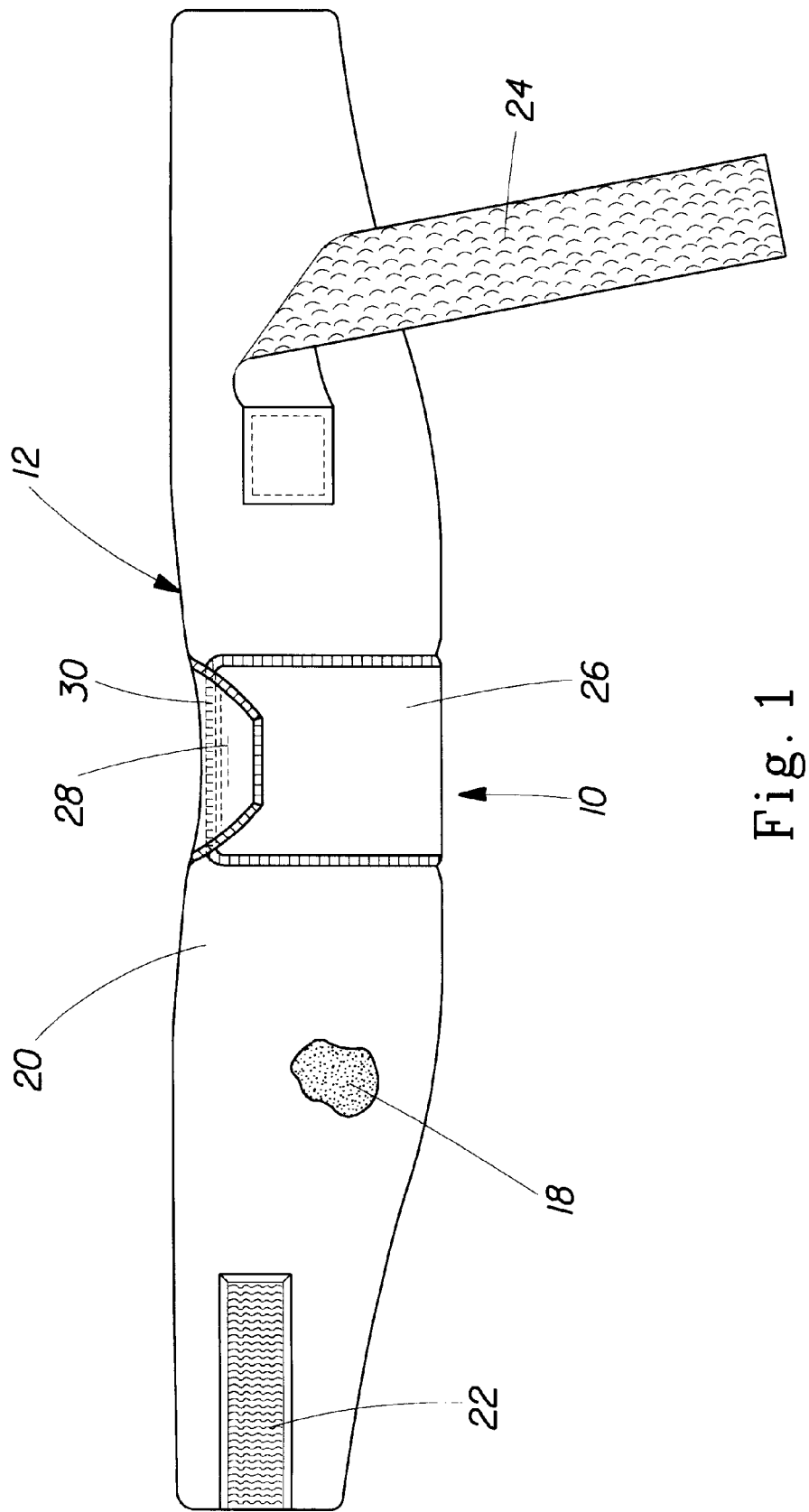
FIG. 1 is a front elevational view of the adjustable cervical collar.
Figure 3:
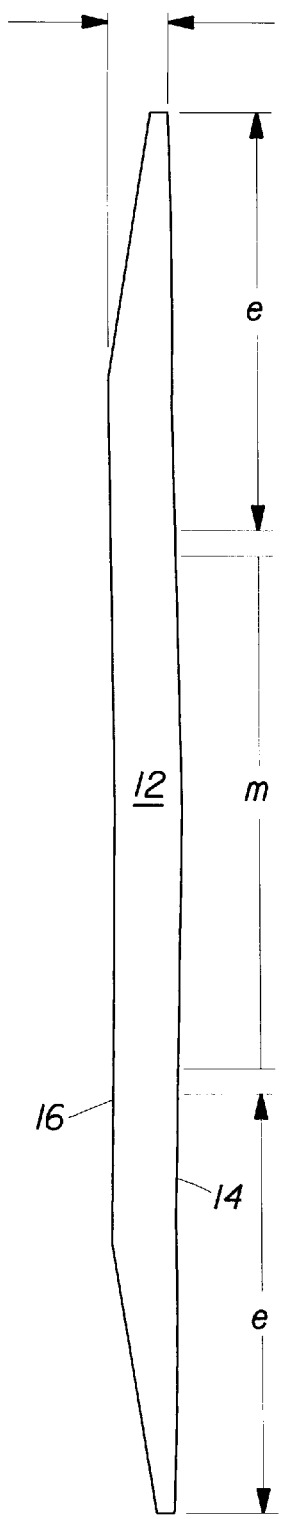
FIG. 3 is a side elevational view of the elongated body member.
Figure 2:
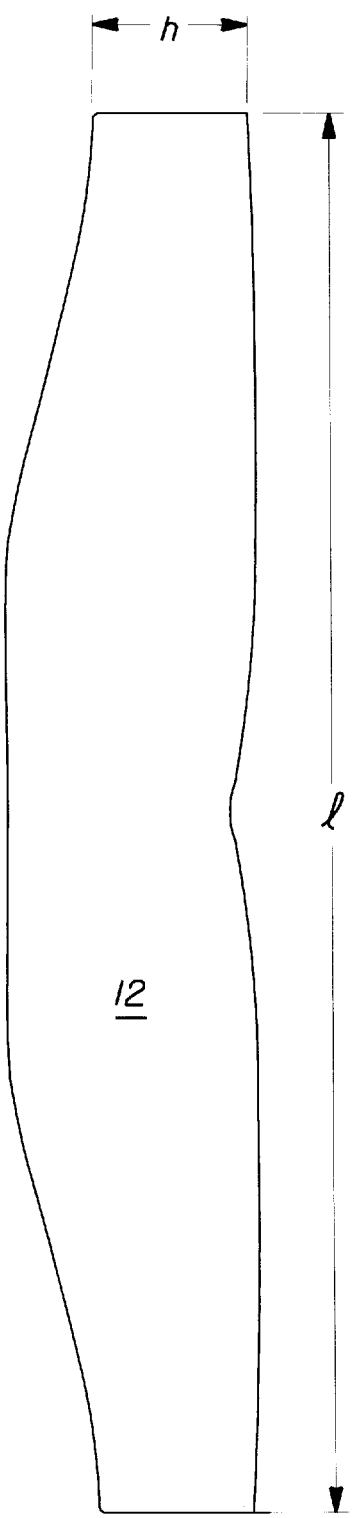
FIG. 2 is a front elevational view of the elongated body member.

As shown in FIG. 1, the cervical collar 10 of the present invention comprises an elongated body member 12. This body member must be of sufficient length 1 to encircle a wearer's neck. See FIGS. 2 and 3. It may be longer than is required to encircle a small neck so that the ends overlap when the body member encircles the neck. However, it is important that it be of sufficient length 1 to encircle a larger than average neck. Typically, the elongated body member 12 is about 18 to about 23 inches long. Preferably, it is about 21.5 inches long. The width w of the elongated body member 12 from the outside surface 16 to the inside surface 14 is typically in the range of about 0.75 to about 1.5 inches thick. Preferably, it is about 1 inch thick.

The height h of the elongated body member 12 at the medial portion, when it is in its uncompressed state, must be sufficient to properly support a longer than average neck. Typically the height h is about 2.5 to about 5 inches high. Preferably, it is 4 inches high. Preferably, the height h of the elongated body member 12 is substantially uniform along in its entire length 1. However, it may be preferable to have the height h at the medial portion of the elongated body member 12 greater than the height at the end portions of the elongated body member. If the height changes along the length of the elongated body member 12, it is preferable that it gradually change in a tapered manner. The height h along the length 1 can change in steps, if so desired.

The elongated body member 12 is comprised of a core 18 and a covering 20. See FIG. 1. The core 18 must be made of a material that is compressible with hand pressure. The core 18 must be elastic in that it will return to its original, uncompressed size and shape when the pressure is released. The core 18 is preferably made of a material that is porous so as to allow heat and moisture to escape from the wearer's neck. More preferably, it is an open cell foam. Such a foam can be thermoset or thermoplastic foam. Preferably, the core is made of polyether-based polyurethane foams, polyester-based polyurethane foams, molded polyurethane foams, visco-elastic foams, neoprene foams, latex foams, polyester fiber foams, rebond foams, or polypropylene foams. More preferably, the core is made of polyether-based polyurethane foams.

Typically, a covering 20 encloses the core 18 such that it substantially conforms to the shape of the core 18. Preferably, it is a stretchable tube with a diameter of about 2.75 to about 3 inches. It is preferable that the covering 20 be porous so as to allow the escape of heat and moisture away from the wearer's neck. The hydrophilicity of the cover 20 may be adjusted so that moisture actually wicks away from the skin. It is also preferable that the covering 20 be wear and abrasion resistant. Preferably, the covering 20 is a knit or woven fabric made from natural or synthetic fibers. More preferably, the fibers are selected from the group consisting of cotton, polyester, rayon, nylon, modacrylic blends, and blends thereof. Most preferably, the covering 20 is a knit fabric made of a cotton/polyester blend.

The cervical collar 10 further comprises fastening means for securing the body member in an encircling relation to the wearer's neck. Any type of fastening means known in the art can be used so long as it provides an adjustable means wherein the overall circumference of the body member can be adjusted. Preferably, the fastening means comprises a hook attachable material 22 on one end portion of the elongated body member 12, and a strip of hook material 24 attached to the other end. The hook attachable material 12 can be the covering 20 on the elongated body member. A hook and loop product, such as Velcro® brand hook and loop material, is preferred because it allows for infinite adjustment of overall circumference, providing the greatest versatility. However, other means including snaps, clasps, etc. could also be used.

Figure 4:
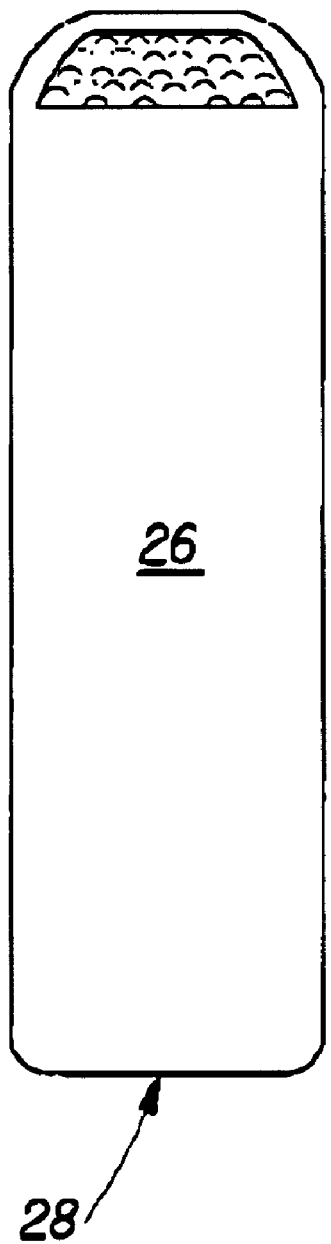
FIG. 4 is an elevational view of the height adjusting means.

As shown in FIGS. 1 and 4, a height adjusting means 26 is attached to the medial portion m of the cervical collar 10. This height adjusting means 26 provides for the compression of the elongated body member 12 at the medial portion so that the overall height h at the medial portion of the collar 10 is modified. Preferably, the height adjusting means 26 comprises a height adjusting band that encircles the medial portion m of the body member 12. Preferably, the band is permanently attached at one end 28 to the medial portion of the body member. It is then wrapped around the medial portion of the body member and is attached to itself. Preferably, the band is about 2 to about 5 inches wide. More preferably, it is about 3 inches wide. The preferred method of attachment is a hook and loop type material. However, any other adjustable attaching means including several straps or snaps at varying heights can be used.

It is important that the band 26 wrap around the medial portion m of the body member 12 and compress it to the desired height h. This height adjusting band 26 must be made of a material that is sufficiently strong to compress the material of the body member 12. The band must be made of a strong, substantially non-stretchable material. It is preferably also soft, hook-engageable, and comfortable against the skin. The band may be made of more than one material. Preferably, the band includes a loop material with a hook attachment 30 at one end so that it provides the greatest versatility with an infinite number of attachment points and, therefore, an infinite number of height adjustments. More preferably, it is made of a cotton duck backing with a foam center about $3/32$" thick and covered with a soft, hook-engageable brushed tricot.

What is claimed:

1. A cervical collar comprising:
    an elongated body member comprising a compressible core, and a fabric covering substantially enclosing the core and conforming substantially to the configuration thereof, said body member having a medial portion and end portions at opposite ends of the medial portion;
    fastening means for securing said body member in encircling relation to a wearer's neck; and,
    a height adjusting band attached to and encircling the medial portion of said body member, said height adjusting band being capable of releasably and adjustably holding the height of the medial portion in a compressed condition.

2. A cervical collar in accordance with claim 1, wherein said elongated body member is about 18 to about 23 inches long, about 0.75 to about 1.5 inches thick and about 2.5 to about 5 inches high.

3. A cervical collar in accordance with claim 2, wherein said elongated body member is about 21.5 inches long.

4. A cervical collar in accordance with claim 2, wherein said elongated body member is about 1 inch thick.

5. A cervical collar in accordance with claim 2, wherein said elongated body member is about 4 inches high.

6. A cervical collar in accordance with claim 1, wherein the height of said elongated body member is substantially uniform along its length.

7. A cervical collar in accordance with claim 1, wherein the height of said elongated body member gradually tapers from the medial portion to the end portions.

8. A cervical collar in accordance with claim 1, wherein the core is made of a thermoset or thermoplastic foam.

9. A cervical collar in accordance with claim 8, wherein the core is porous.

10. A cervical collar in accordance with claim 9, wherein the core is made of an open cell foam.

11. A cervical collar in accordance with claim 8, wherein the core is made of a material selected from the group consisting of polyether-based polyurethane foams, polyester-based polyurethane foams, molded polyurethane foams, visco-elastic foams, neoprene foams, latex foams, polyester fiber foams, rebond foams, and polypropylene foams.

12. A cervical collar in accordance with claim 11, wherein the core is made of polyether-based polyurethane foams.

13. A cervical collar in accordance with claim 1, wherein the fabric covering is a stretchable tube with a diameter of about 2.75 to about 3 inches.

14. A cervical collar in accordance with claim 1, wherein the fabric covering is porous.

15. A cervical collar in accordance with claim 1, wherein the fabric covering is a knit or woven fabric.

16. A cervical collar in accordance with claim 15, wherein the fabric covering is made from natural or synthetic fibers.

17. A cervical collar in accordance with claim 16, wherein the fabric covering is made of a material selected from the group consisting of cotton, polyester, rayon, nylon, modacrylic blends, and blends thereof.

18. A cervical collar in accordance with claim 17, wherein the fabric covering is a knit fabric made of a cotton/polyester blend.

19. A cervical collar in accordance with claim 1, wherein the fastening means comprises a hook engageable material located at one end portion and a strip of hook material located at the other end portion.

20. A cervical collar in accordance with claim 1, wherein said height adjusting band is about 2 to about 5 inches wide.

21. A cervical collar in accordance with claim 20, wherein said height adjusting band is about 3 inches wide.

22. A cervical collar in accordance with claim 1, wherein said height adjusting band is permanently attached at one of its ends to said elongated body member so that it can be wrapped around the medial portion of said elongated body member and attached to itself at its other end.

23. A cervical collar in accordance with claim 22, wherein said height adjusting band comprises a soft, hook engageable material that is comfortable against a wearer's skin.

24. A cervical collar in accordance with claim 22, wherein said height adjusting band has a hook engageable material at the end that is not permanently attached to said elongated body member.

25. A cervical collar in accordance with claim 24, wherein said height adjusting band comprises a cotton duck backing with a foam center that is covered with a soft, hook-engageable brushed tricot.

* * * * *